United States Patent [19]

Muhler et al.

[11] 4,400,372

[45] Aug. 23, 1983

[54] CHEWING GUM

[75] Inventors: Joseph C. Muhler, Howe; Carl J. Kleber, Fort Wayne, both of Ind.; Ronald L. Ream, North Aurora; David M. Moore, Lombard, both of Ill.

[73] Assignee: Indiana University Foundation, Bloomington, Ind.

[21] Appl. No.: 339,754

[22] Filed: Jan. 15, 1982

Related U.S. Application Data

[63] Continuation-in-part of Ser. No. 240,793, Mar. 4, 1981.

[51] Int. Cl.$^3$ ................................................ A61K 9/68
[52] U.S. Cl. ........................................... 424/48; 426/3
[58] Field of Search .................. 424/48, 49, 52; 426/3

[56] References Cited

U.S. PATENT DOCUMENTS

| | | | |
|---|---|---|---|
| 1,592,013 | 7/1926 | Taylor | 424/48 |
| 2,059,396 | 11/1936 | Ripert | 424/52 |
| 3,105,013 | 9/1963 | Saul et al. | 424/52 |
| 3,282,792 | 11/1966 | Fiscella | 424/52 |
| 3,378,445 | 4/1968 | Muhler | 424/49 |
| 3,590,120 | 6/1971 | Muhler | 424/48 |
| 4,108,979 | 8/1978 | Muhler et al. | 424/52 |
| 4,108,981 | 8/1978 | Muhler et al. | 424/52 |
| 4,122,163 | 10/1978 | Muhler et al. | 424/52 |
| 4,151,270 | 4/1979 | Ream | 424/48 |
| 4,153,732 | 5/1979 | Muhler et al. | 424/48 |

*Primary Examiner*—Shep K. Rose
*Attorney, Agent, or Firm*—Kirkland & Ellis

[57] ABSTRACT

An improved chewing gum capable of cleaning and imparting a high degree of polish to the teeth comprises a chewing gum base, at least one non-toxic source of acid, and calcined kaolin particles, the median diameter of which is about 2 micrometers or less, substantially all of the particles being less than about 20 micrometers in diameter. Such a chewing gum cleans and imparts a high degree of polish to the teeth without unduly abrading or scratching them. When regularly chewed, such a gum, in addition to cleaning and polishing the dental enamel, also inhibits the reformation of dental plaque.

12 Claims, No Drawings

CHEWING GUM

CROSS REFERENCE TO RELATED PATENTS

The present application is a continuation-in-part of applicants' copending United States patent application, Ser. No. 240,793, filed Mar. 4, 1981.

BACKGROUND OF THE INVENTION

1. Field of the Invention

The present invention relates to chewing gum compositions and especially chewing gum compositions incorporating in combination at least one non-toxic source of acid and calcined kaolin particles capable of cleaning and imparting a high degree of polish to the teeth and of reducing the rate of dental plaque formation.

2. Description of the Prior Art

Dental research has developed substantial evidence that dental plaque is the predominant etiological factor responsible for both periodontal disease and dental caries. Dental caries is the localized, progressive decay of the teeth. It results from tooth demineralization brought about by acids formed when bacteria in dental plaque ferment carbohydrate foods present in the mouth.

With the discovery of fluorides, advances have been made in the reduction of dental caries. However, this progress has been somewhat offset for a variety of reasons, among them the increased intake of sugar-containing processed foods and snacks, as well as poor oral hygiene habits and attitudes. In fact dental caries, which afflicts more than 95% of Americans by the time they become adults, is the most prevalent disease in the United States with the exception of the common cold.

After the age of 35, the main cause of tooth loss is due to periodontal disease. The most important single factor contributing to periodontal disease is the accumulation of plaque and dental calculus (e.g., salivary tartar) on the teeth. These deposits result in tissue inflammation of the surrounding gingiva, and, as the condition increases in severity, the supporting bone is also affected. These reactions lead to the destruction of the supporting structures and the subsequent mass loss of teeth which are usually free of decay.

Although brushing the teeth with a toothbrush and dentifrice is a widely recognized technique for maintaining dental health, the average American brushes only about once a day for approximately one minute. Therefore, a great need exists for finding additional methods for improving daily oral hygiene. Chewing gum has over the years been advocated as a possible excellent adjunct for cleaning the teeth because people find the chewing of gum very pleasurable and chew gum for much longer periods of time than they brush their teeth. Chewing gum is especially advantageous for use in circumstances where toothbrushing is not possible or convenient, such as after lunch, while traveling, or while working. However, while mastication of conventional chewing gum is known to be capable of reducing the amount of debris on and between the teeth, gum chewing has been shown to be incapable of removing dental plaque, calculus or stain from the teeth without added therapeutic agents. And, while chewing gums have often been proposed as vehicles for the administration of dental therapeutic agents such as fluorides, phosphates, enzymes, and other materials, none of these systems has been made commercially available because of insufficient supporting data or toxicological problems.

The concept of high enamel polish is recognized to be critical to good oral hygiene because smooth, polished tooth surfaces have fewer nidi or sites to which oral bacteria adhere than do unpolished, rough enamel surfaces. The primary reason dental caries and periodontal disease develop is that such bacteria adhere to and grow on enamel surfaces. By physically polishing the dental enamel, the potential for bacteria colonization on the teeth is reduced, less bacterial plaque is formed, and, consequently, dental caries and periodontal disease are inhibited. The high polished concept, thus, would offer a significant approach to the prevention of dental plaque and exogenous stain if a proper vehicle for its application could be developed.

Available dentifrice abrasives have, when employed in dentifrices, exhibited relatively unsatisfactory enamel polishing qualities and consequently have not been wholly effective in preventing the re-accumulation of materia alba, oral debris, plaque, pellicle, stains, and dental calculus.

In particular, while conventional cleaning and polishing agents used with a toothbrush are capable, to varying degrees, of removing materia alba, food particles, exogenous stains, and other tooth surface pigmentations when utilized in ordinary daily brushings, they are generally ineffective in removing the more resistant forms of enamel pigments and usually lack the polishing characteristics necessary to produce a smooth surface that is resistant to plaque and dental calculus reformation.

In fact, conventional agents often are quite abrasive to the tooth surfaces and tend to erode the tooth enamel and the surrounding soft dentin areas. This abrasion leaves a rough tooth surface that actually facilitates the re-accumulation of pellicle (the precursor to dental stains) and plaque (the precursor to dental caries, periodontal disease and calculus). Furthermore, these conventional dental abrasives leave the teeth aesthetically less desirable than would more effective polishing agents.

A chewing gum capable of cleaning and polishing the teeth is disclosed in U.S. Pat. No. 3,590,120 granted June 29, 1971 to the assignee of this application. That patent describes the addition to a chewing gum during its formulation of zirconium silicate ($ZrSiO_4$) of highly specific particle size and surface configuration. While chewing gums produced in accordance with U.S. Pat. No. 3,590,120 have polished the teeth with good success, because zirconium silicate is a hard mineral, the teeth have also been scratched slightly. In addition, zirconium silicate is slightly radioactive, a factor which has also limited application of the techniques of the U.S. Pat. No. 3,590,120. U.S. Pat. No. 3,590,120 also suggests that zirconium silicate may be combined with other abrasives such as kaolinite but does not recognize that kaolinite must be calcined in order to impart high polish to the teeth.

The use of calcined kaolin as a dentifrice abrasive in combination with fluoride is known from U.S. Pat. No. 4,122,163, also assigned to applicants' assignee. That patent is concerned with the application of highly purified calcined kaolin in dentifrices but does not recognize the existence of any other potential applications in the oral hygiene field.

Accordingly, it is a primary object of the present invention to provide a chewing gum capable of removing dental plaque and of imparting a high degree of polish to the teeth.

Another object is to provide a chewing gum capable of cleaning and polishing the teeth without unduly abrading or scratching the enamel surface.

A still further object is the provision of a new dental cleaning and polishing system which may be incorporated into chewing gums in order to permit successful application of the high polish oral hygiene concept.

A still further object is to provide methods of polishing the teeth and inhibiting the formation of dental plaque by using chewing gum compositions of the character described.

SUMMARY OF THE INVENTION

The foregoing other objects, advantages and features of this invention may be achieved with chewing gum compositions capable of cleaning and imparting a high degree of polish to the teeth which comprise a chewing gum base; at least one non-toxic source of acid; and calcined kaolin particles, the median diameter of which is about 2 micrometers or less, substantially all of the particles being less than 20 micrometers in diameter.

The calcined kaolin particles are provided in a range of about 1–50%, preferably 5–15% by weight of the chewing gum. The calcined kaolin may be employed as a filler incorporated during formulation of the gum base, as a component of the solubles added during production of the chewing gum, or as a combination thereof.

The non-toxic source of acid is preferably provided at an effective level, preferably at a level sufficient to produce an aqueous pH ranging from about 2.6 to about 3.3 when measured in a solution with a concentration of 0.1 gram of chewing gum to 1 milliliter of demineralized water. The acid is essential to achieving a high degree of polish in accordance with this invention.

The acid source may be one or more organic acids, inorganic acids or acid salts thereof. Suitable non-toxic acids which may be employed in accordance with this invention include organic acids such as saturated and unsaturated, hydroxy and non hydroxy $C_1$ to $C_6$ mono-, di- and tribasic carboxylic acids such as citric acid, fumaric acid, tartaric acid, malic acid, succinic acid, ascorbic acid, glutaric acid, adipic acid, lactic acid, hydroxyacetic acid and mixtures thereof. Among the inorganic acids that may be used in accordance with this invention are phosphoric acid, perchloric acid, nitric acid, hydrochloric acid, sulfuric acid and boric acid. Suitable acid salts include alkali and alkaline earth metal salts of the foregoing acids, such as monobasic calcium phosphate, monobasic sodium phosphate, sodium hydrogen sulfite and sodium pyrophosphate.

In its method aspect, regular chewing of a chewing gum of the character described permits a high degree of polish to be imparted to the oral hard tissues and allows dental plaque to be removed from the dental surfaces. Regular chewing in accordance with this invention also reduces the rate of dental plaque reformation.

DESCRIPTION OF THE PREFERRED EMBODIMENTS

In accordance with the present invention, it has been found that an improved chewing gum capable of imparting a high degree of polish to the teeth may be obtained by providing in combination a chewing gum base, at least one non-toxic source of acid, and calcined kaolin particles, the median diameter of which is about 2 micrometers or less, substantially all of the particles being less than 20 micrometers in diameter.

The kaolin particles are provided in the chewing gum at a level of about 1–15% by weight of the over all chewing gum. (Unless otherwise indicated, all amounts and proportions given herein are expressed in terms of the total weight of the chewing gum.) Preferably, the kaolin is provided at a level of about 5–15% by weight.

The calcined kaolin particles of this invention may be obtained by calcining (i.e., heat treating) kaolinite, [$Al_4Si_4O_{10}(OH)_8$], which has been mined, cleaned, dried, and fractionated. Prior to calcining, the material may be subjected to a purification procedure, such as the flocculation and related steps described in U.S. Pat. No. 3,477,809.

The kaolin is preferably calcined at a temperature lying in the range of about 1000° C. to 1100° C. If the temperature does not reach 1000° C., the kaolinite remains predominantly meta-kaolin, a material which is insufficiently hard for cleaning and polishing satisfactorily from a dental standpoint. Material which has been calcined at about 1000° C. is predominantly gamma alumina. If the purified material is over calcined, (i.e., is subjected to temperatures above about 1100° C.), the gamma alumina undergoes a change to highly crystalline mullite ($3Al_2O_3.2SiO_2$), generally taking the form of small, needle-like crystals, or cristobolite ($SiO_2$). Material containing large amounts of cristobolite and mullite crystals are unsatisfactory from a dental standpoint because of their tendency to scratch the tooth enamel. As a consequence, the calcined kaolins employed with this invention are preferably predominantly of the gamma alumina form.

After calcining, during which the kaolin agglomerates into large masses, grinding and/or milling must be used to obtain a polishing agent having a particle size distribution lying in the range found to be useful from a dental standpoint. Conventional milling procedures, including Bauer-milling, wet sand grinding and the like, may be used.

The kaolin particles should not be present in the chewing gum in sizes substantially in excess of 20 micrometers in diameter because such larger particles are detectable as "grit" in the mouth. The median particle size may be varied without significantly affecting the polishing capability of the chewing gum although somewhat larger particles (up to about 10 micrometers median diameter) exhibit marginally improved polishing capabilities as compared to smaller median particles. However, in order to guard against undesirable abrasion or scratching of the enamel, it is important that the particle size of the calcined kaolin particles be carefully controlled. Where the median size of the calcined kaolin particles lie in a range of up to about 2 micrometers, no undue abrasion is encountered. Such kaolins exhibit abrasion measurements comparable to those of acceptable standard dentifrice abrasives.

Optimal results from both a polishing and abrasion standpoint are achieved with the largest median particle size distribution that can be employed consistent with acceptable abrasion scores. In accordance with this invention, a preferred particle size distribution meeting these criteria is given in Table I.

TABLE 1

| CALCINED KAOLIN PARTICLE SIZE | |
|---|---|
| Particle Size (Micrometers) | Weight (%) |
| 0–3 | 70 |

TABLE 1-continued

| CALCINED KAOLIN PARTICLE SIZE | |
|---|---|
| Particle Size (Micrometers) | Weight (%) |
| 3–5 | 15 |
| 5–10 | 10 |
| 10–20 | 5 |
| >20 | 0 |

As noted, the kaolin particles are provided at a level of about 1–50%, preferably 5–15% by weight of the overall gum composition. The calcined kaolin particles may be supplied as an add-on ingredient during the actual production of the finished chewing gum or, alternatively, may be incorporated in the gum base in replacement of all or a portion of the filler constituents. A combination of such techniques may also be employed, but it is preferred to employ the calcined kaolin particles at least in part as an add-on component.

For example, the gum may advantageously contain up to about 50% kaolin filler by weight of the gum base component and up to about 50% add-on-ingredient by total gum weight. Where calcined kaolin is present as both filler and add-on-ingredient, about 5–30% by weight of the gum base is provided as filler and the balance up to about 50% by total gum weight is present as add-on ingredient.

As noted, it is essential to provide a non-toxic source of acid in combination with the kaolin particles in order to achieve the high levels of dental enamel polish with the present invention. Among the acid sources which may be employed in accordance with this invention are organic acids, inorganic acids and acid salts. Suitable non-toxic organic acids which may be employed include saturated and unsaturated, hydroxy and non-hydroxy, $C_1$ to $C_6$ mono-, di- and tribasic carboxylic acids. Suitable carboxylic acids include naturally occurring and commonly used food acids such as citric acid, fumaric acid, tartaric acid, malic acid, succinic acid, ascorbic acid, glutaric acid, adipic acid, lactic acid, and hydroxyacetic acid. Suitable inorganic acids include phosphoric acid, perchloric acid, nitric acid, hydrochloric acid, sulfuric acid and boric acid. Suitable acid salts include alkalai and alkaline earth metal salts of the foregoing acids. Preferred acid salts include monobasic calcium phosphate, monobasic sodium phosphate, sodium pyrophosphate and sodium hydrogen sulfite. Mixtures of acids and salts may also be employed.

Although chewing gum containing calcined kaolin particles without a source of acid polish the teeth somewhat better than a control gum containing no kaolin particles, the most dramatic increases in dental enamel polish are obtained when an effective amount of a non-toxic acid is present in the gum with the kaolin. Improved polish is achieved with substantially any perceptible amounts of acid. Polishing effectiveness may be doubled, however, by employing a source of acid in a concentration that yields an aqueous pH in the range of about pH 2.6 to 3.3.

The acid components in general should be provided at a level greater than 0 up to about 3% by weight so as to provide an aqueous pH in the range of about 2.6 to 3.3.

Increasing the amounts of acid to higher levels above about 3% by weight may in the case of certain acids result in a loss of enamel polish believed to be caused by dulling of the dental enamel by the high acid content. In the case of other acids (e.g., ascorbic acid, glutaric acid, succinic acid and especially adipic acid) adverse taste limits the acid to a maximum of about 3.0% by weight. If taste considerations are overcome, more than 3.0% by weight of such acids may be used.

The taste of inorganic acids and especially the taste of the acid salts of phosphoric acid is more easily masked than is the taste of carboxylic acids. Since inorganic acids are in all other respects equally well-suited to use in a calcined kaolin chewing gum, inorganic acids are preferable to carboxylic acids where taste considerations require that the acid taste be masked. Tart fruit flavored gums, however, do not require masking of the acid taste and carboxylic acids are therefore preferred to inorganic acids for such gums.

The acid source is incorporated in a conventional chewing gum base comprising calcined kaolin. Suitable chewing gum bases may be obtained from commercial suppliers. Suitable raw materials for gum bases which may be employed in accordance with this invention include chicle, latex, RBH resin, ester gum, petroleum waxes, rosins, crown gum, Malsa compound, PU-C, picllylite resin, candelilla wax, chiquibil gum, polyvinyl acetate, styrene butadiene, and the like. Most gum bases prepared without any calcium carbonate as filler are generally suitable although, as will hereinafter be demonstrated, some bases particularly enhance the cleaning and polishing characteristics of the calcined kaolin-containing gums.

Suitable conventional stick gum bases (i.e., as opposed to bubble gum bases) include "Paloja T"; "Firm Paloja T"; and "Nova T". Suitable bubble gum bases include; "Paloja Bubble T"; "Ladco Bubble T"; and "Grande Bubble T". All of these bases are commercially available from the L.A. Dreyfus Corporation, P.O. Box 500, South Plainfield, N.J. 07080.

The gum base is normally employed at a level of about 10–60 percent of total gum weight. Advantageously, the gum base is about 15–30%, preferably about 18–26%, of the overall gum composition.

In addition to the calcined kaolin particles, non-toxic source of acid, and gum base, as described, chewing gums in accordance with this invention comprise excipients such as corn syrup, sucrose, sorbitol, xylitol and other flavoring and sweetening agents as well as various inert filler materials. In accordance with this invention, it is preferred that the gums be formulated without sucrose or other cariogenic sweetening agents. Such gums may be prepared in several possible forms such as conventional stick gum, bubble gums, and the like.

The excipient constituents of the gum may include any of the conventional flavoring and sweetening components to a level in the range of about 30–80% by total gum weight. Flavors such as spearmint, peppermint, wintergreen, fruit flavors, and the like may be used. The preferred gum compositions employ non-cariogenic sweetening systems using natural and synthetic sweetening agents rather than corn syrup and sugar because of the cariogenic potential of natural sweeteners.

Inert filling ingredients, such as talc, sorbitol, mannitol, glycerin, lecithin, or the like are provided in the gum base in order to contribute to the over-all consistency of the composition.

The foregoing gum bases, excipients, and fillers are all known chewing gum constituents and are provided at conventional levels and therefore per se form no part of the present invention.

In all cases, the gum base and other constituents used should be non-acidophilic (i.e., they should be inert to acid attack or otherwise unreactive with the acid constituent). Thus, gums containing calcium carbonate as a filler, for example, cannot be successfully employed since the acid reacts in situ with calcium carbonate and causes the gum upon chewing to crumble and loose texture and neutralizes the high polishing efficacy of the gum.

The calcined kaolin particles and acid source may be incorporated in the chewing gum in any convenient manner during the manufacture thereof. In particular, calcined kaolin particles may be present as a part of the filler employed in formulating the chewing gum base, or it may be provided later when the chewing gum is formulated. Preferably, the calcined kaolin particles and food acid are provided at least in part as an add-on ingredient to the chewing gum. Likewise, the source of acid may be provided in the formulation of the chewing gum base or it may be provided as an add-on ingredient.

An exemplary method for formulating a chewing gum in accordance with this invention is given in the following example.

EXAMPLE I

Conventional chewing gum manufacturing techniques are used in preparing regular and sugarless chewing gums, and no process variations need be made. The calcined kaolin present as add-on is most advantageously incorporated early in the gum preparation. In preparing a sugarless gum, 260 grams of chewing gum base containing 29.5% calcined kaolin as filler is placed in an unheated sigma mixer and agitated for a few minutes. All the calcined kaolin add-on (23.3 g) and about one-half the powdered sorbitol (250 g) are then added and allowed to mix for five minutes. Next, all the glycerin (20 g) and one-third of the sorbitol solution (60 g) are added to the mixer. After five minutes, one-half each of the remaining sorbitol powder (118 g) and sorbitol solution (55 g) are blended in. After an additional five minutes, the balance of the sorbitol solution (55 g) and sorbitol powder (118.7 g) are added to the gum. Finally, the source of acid (30 g) and flavor (10 g) are slowly added and allowed to blend thoroughly in the gum.

The finished gum is then removed from the sigma mixer, shaped into the desired form such as stick form, dusted with mannitol or starch, and allowed to cool, after which it may be wrapped and packaged. When preparing sugar-containing gums, it is necessary to heat the mixer while following the aforementioned procedure.

Compositions of other exemplary chewing gums in accordance with the present invention are given in the following examples.

EXAMPLE II

| Constituent | Parts By Weight |
| --- | --- |
| Chewing gum base containing 29.5% calcined kaolin filler | 26.0 |
| Sorbitol powder | 48.7 |
| Sorbitol solution (70% aqueous solution) | 17.0 |
| Glycerin | 2.0 |
| Calcined kaolin | 2.3 |
| Adipic acid | 3.0 |
| Flavoring (mixed fruit) | 1.0 |
| | 100.0 |

EXAMPLE III

| Constituent | Parts By Weight |
| --- | --- |
| Paloja T gum base | 19.4 |
| Corn syrup | 19.8 |
| Powdered sugar | 47.3 |
| Glycerin | 0.5 |
| Calcined kaolin | 10.0 |
| Lactic acid | 2.0 |
| Flavor | 1.0 |
| | 100.0 |

EXAMPLE IV

| Constituent | Parts By Weight |
| --- | --- |
| Paloja Bubble T base | 26.0 |
| Sorbitol powder | 36.8 |
| Sorbitol (70% aqueous solution) | 15.0 |
| Glycerin | 4.5 |
| Kaolin (calcined 1000° C., 1.8 micrometer median particle size) | 15.0 |
| Citric acid | 1.0 |
| Adipic acid | 1.0 |
| Flavor (guarana) | 0.7 |
| | 100.0 |

EXAMPLE V

| Constituent | Parts By Weight |
| --- | --- |
| Nova T gum base | 25.0 |
| Sorbitol powder | 44.5 |
| Sorbitol (70% aqueous solution) | 15.0 |
| Glycerin | 4.5 |
| Kaolin (calcined 1050° C., 1.2 micrometer median particle size) | 8.0 |
| Tartaric acid | 1.5 |
| Flavor (grape) | 1.5 |
| | 100.0 |

EXAMPLE VI

| Constituent | Parts By Weight |
| --- | --- |
| Paloja T gum base | 25.0 |
| Sorbitol powder | 46.5 |
| Sorbitol (70% aqueous solution) | 15.0 |
| Glycerin | 4.5 |
| Kaolin (calcined 1100° C., 0.8 micrometer median particle size) | 5.0 |
| Fumaric acid | 1.0 |
| Ascorbic acid | 2.0 |
| Flavor (orange) | 1.0 |
| | 100.0 |

EXAMPLE VII

| Constituent | Parts By Weight |
| --- | --- |
| Grande Bubble T | 26.0 |
| Sorbitol powder | 31.5 |
| Sorbitol (70% aqueous solution) | 15.0 |
| Glycerin | 4.5 |
| Kaolin (calcined 1050° C., 0.2 micrometer median particle size) | 20.0 |
| Malic acid | 2.0 |
| Flavor (apple) | 1.0 |
| | 100.0 |

EXAMPLE VIII

| Constituent | Parts By Weight |
|---|---|
| Ladco Bubble T | 16.8 |
| Corn syrup | 22.4 |
| Powdered sugar | 48.2 |
| Glycerin | 0.3 |
| Water | 0.3 |
| Kaolin (calcined 1050° C., 1.5 micrometer median particle size) | 10.0 |
| Glutaric acid | 0.5 |
| Citric acid | 0.5 |
| Flavor | 1.0 |
| | 100.0 |

EXAMPLE IX

| Constituent | Parts By Weight |
|---|---|
| Bubble Gum base containing 20.0% calcined kaolin filler | 26.0 |
| Sorbitol powder | 49.5 |
| Sorbitol (70% aqueous solution) | 15.0 |
| Glycerin | 4.5 |
| Kaolin (calcined 1100° C., 1.0 micrometer median particle size) | 3.0 |
| Succinic acid | 1.0 |
| Flavor (peppermint) | 1.0 |
| | 100.0 |

EXAMPLE X

| Constituent | Parts By Weight |
|---|---|
| Chewing Gum base containing 40.0% calcined kaolin filler | 30.0 |
| Sorbitol powder | 49.3 |
| Sorbitol (70% aqueous solution) | 15.0 |
| Glycerin | 4.5 |
| Adipic acid | 0.2 |
| Flavor (spearmint) | 1.0 |
| | 100.0 |

EXAMPLE XI

| Constituent | Parts by Weight |
|---|---|
| Chewing gum base containing 29.5% calcined kaolin filler | 26.0 |
| Sorbitol powder | 48.7 |
| Sorbitol solution (70% aqueous solution) | 17.0 |
| Gylcerin | 3.0 |
| Calcined kaolin | 2.3 |
| Hydrochloric acid (2M aqueous solution) | 2.0 |
| Flavor (peppermint) | 1.0 |
| | 100.0 |

EXAMPLE XII

| Constituent | Parts by Weight |
|---|---|
| Paloja T gum base | 19.4 |
| Corn syrup | 10.8 |
| Powdered sugar | 49.0 |
| Glycerin | 0.5 |
| Calcined kaolin | 10.0 |
| Phosphoric acid (85% aqueous solution) | 0.3 |
| Flavor (spearmint) | 1.0 |
| | 100.0 |

EXAMPLE XIII

| Constituent | Parts by Weight |
|---|---|
| Paloja Bubble T base | 26.0 |
| Sorbitol powder | 37.7 |
| Sorbitol (70% aqueous solution) | 15.0 |
| Glycerin | 4.5 |
| Kaolin (calcined 1000° C., 1.8 micrometer median particle size) | 15.0 |
| Sulfuric acid (96% aqueous solution) | 0.1 |
| Boric acid (3M) | 1.0 |
| Flavor (guarana) | 0.7 |
| | 100.0 |

EXAMPLE XIV

| Constituent | Parts by Weight |
|---|---|
| Nova T gum base | 25.0 |
| Sorbitol powder | 45.8 |
| Sorbitol (70% aqueous solution) | 15.0 |
| Glycerin | 4.5 |
| Kaolin (calcined 1050° C., 1.2 micrometer median particle size) | 8.0 |
| Nitric acid (70% aqueous solution) | 0.2 |
| Flavor (mint) | 1.5 |
| | 100.0 |

EXAMPLE XV

| Constituent | Parts by Weight |
|---|---|
| Paloja T gum base | 25.0 |
| Sorbitol powder | 49.1 |
| Sorbitol (70% aqueous solution) | 15.0 |
| Glycerin | 4.5 |
| Kaolin (calcined 1100° C., 0.8 micrometer median particle size) | 5.0 |
| Hydrochloric acid (37% aqueous solution) | 0.3 |
| Adipic acid | 0.1 |
| Flavor (orange) | 1.0 |
| | 100.0 |

EXAMPLE XVI

| Constituent | Parts by Weight |
|---|---|
| Grande Bubble T | 26.0 |
| Sorbitol powder | 33.2 |
| Sorbitol (70% aqueous solution) | 15.0 |
| Glycerin | 4.5 |
| Kaolin (calcined 1050° C., 0.2 micrometer median particle size) | 20.0 |
| Perchloric acid (70% aqueous solution) | 0.3 |
| Flavor (peppermint) | 1.0 |
| | 100.0 |

EXAMPLE XVII

| Constituent | Parts by Weight |
|---|---|
| Ladco Bubble T | 16.8 |
| Corn syrup | 22.4 |
| Powdered sugar | 49.0 |
| Glycerin | 0.3 |
| Water | .3 |
| Kaolin (calcined 1050° C., 1.5 micrometer median particle size) | 10.0 |
| Phosphoric acid (85% aqueous solution) | 0.1 |
| Sodium acid pyrophosphate | 0.1 |

-continued

| Constituent | Parts by Weight |
|---|---|
| Flavor (wintergreen) | 1.0 |
| | 100.0 |

EXAMPLE XVIII

| Constituent | Parts by Weight |
|---|---|
| Bubble Gum base containing 20.0% calcined kaolin filler | 26.0 |
| Sorbitol powder | 50.2 |
| Sorbitol (70% aqueous solution) | 15.0 |
| Glycerin | 4.5 |
| Kaolin (calcined 1100°, 1.0 micrometer median particle size) | 3.0 |
| Sodium bisulfate | 0.2 |
| Monobasic calcium phosphate | 0.1 |
| Flavor (peppermint) | 1.0 |
| | 100.0 |

EXAMPLE XIX

| Constituent | Parts by Weight |
|---|---|
| Chewing Gum base containing 40.0% calcined kaolin filler | 30.0 |
| Sorbitol powder | 49.2 |
| Sorbitol (70% aqueous solution) | 15.0 |
| Glycerin | 4.5 |
| Phosphoric acid (85% aqueous solution) | 0.2 |
| Monobasic sodium phosphate | 0.1 |
| Flavor (spearmint) | 1.0 |
| | 100.0 |

EXAMPLE XX

| Constituent | Parts by Weight |
|---|---|
| Chewing Gum base containing 10.0% calcined kaolin filler | 25.0 |
| Sorbitol powder | 46.6 |
| Sorbitol (70% aqueous solution) | 15.0 |
| Glycerin | 4.5 |
| Hydroxyacetic acid | 0.1 |
| Phosphoric acid (85% aqueous solution) | 0.1 |
| Calcined kaolin | 8.0 |
| Flavor (peppermint) | 0.7 |
| | 100.0 |

EXAMPLE XXI

| Constituent | Parts by Weight |
|---|---|
| Chewing Gum base containing 10.0% calcined kaolin filler | 25.0 |
| Sorbitol powder | 46.58 |
| Sorbitol (70% aqueous solution) | 15.0 |
| Glycerin | 4.5 |
| Hydroxyacetic acid | 0.08 |
| Phosphoric acid (85% aqueous solution) | 0.08 |
| Monobasic calcium phosphate | 0.07 |
| Calcined kaolin | 8.0 |
| Flavor (peppermint) | 0.7 |
| | 100.0 |

Each of the foregoing examples may be modified by employing different combinations of non-toxic acid source and calcined kaolin particles in accordance with this invention.

EXPERIMENTAL EVALUATIONS

The effectiveness of the high polish chewing gum obtained in accordance with the present invention has been demonstrated by in vitro studies concerning the polishing and abrasion characteristics of such chewing gums. In addition, the effectiveness of chewing gums in accordance with this invention in removing dental plaque has been evaluated in vivo in human clinical studies.

The polishing and abrasion characteristics of experimental and commercial chewing gums have been evaluated using a device that simulates the mastication of chewing gum in the oral cavity using two occluding teeth and a saliva medium maintained at the 37° C. body temperature. This device is described in Kleber, Schimmele, Putt & Muhler, *A Mastication Device Designed for the Evaluation of Chewing Gums*, J.Dent.Res. 60:109 (1981).

This device consists essentially of a heat regulated 40 ml-capacity reservoir, a motorized reciprocating shaft, and two paddles. The reservoir has a machined 2 cm square depression in the center for accomodating a tooth specimen. A set screw locks the tooth specimen into the reservoir depression. The reservoir also serves to hold the chewing gum and saliva during testing. Two holes in the base of the reservoir accomodate a rheostatically-controlled heating element and thermocouple, which are used to maintain the gum and saliva at 37° C. The entire reservoir assembly is held firmly in place by means of two thumb bolts and can be easily removed for cleaning.

The reciprocating shaft is attached at one end to an offset pin on a 40-tooth gear. This gear is meshed to an 80-tooth gear driven by a 1/120 HP electric motor. (Model 27808, Dayton Electric Mfg. Co., Chicago, Ill. 60647) This 2:1 gear ratio generates a running torque of 35.0 kg-cm. Rotation of the gears causes the shaft to repeatedly move in and out of the reservoir at a rate of fifty cycles per minute. The free end of the shaft is fitted with a removable holder, which enables a second tooth specimen to be mounted on the end of the shaft. On the descending stroke, the upper tooth in the holder occludes with the lower tooth mounted in the reservoir. In addition, a special adjustable sleeve surrounds the center of the shaft and converts the up and down motion of the shaft into a rocking motion of the moment of occlusion, thus simulating masticatory shearing.

The two paddles simulate the action of the cheeks and tongue by repositioning the gum over the tooth in the reservoir after each chewing cycle. The center of each paddle is mounted on a pin attached to the frame on either side of the reciprocating shaft. The top ends of the paddles are connected by a steel spring which holds them adjacent to an eliptical cam mounted on the motorized gear. The other two ends of the paddles fit into the reservoir and contain inert resin pieces that are flush with the bottom and sides of the reservoir. On the descending stroke, the eliptical cam releases the spring loaded top portion of the paddles which in turn causes the opposite end of the paddles to open. As the shaft ascends at the end of the chewing cycle, the eliptical cam pushes the top portion of the spring loaded paddles apart, thus forcing the two inert resin pieces on the opposite end to come together and reposition the gum over the tooth in the reservoir in preparation for the next chewing cycle.

A mechanical trip counter mounted on the side of the device automatically records the number of chewing cycles. The device is also equipped with on-off switches for both the motor and heating system. All metal parts are constructed from hospital grade stainless steel to resist corrosion.

The method for determining the enamel polish of chewing gums using the mastication device is as follows. First, the heating element is turned on in order to warm the saliva reservoir to body temperature. Next, the upper and lower tooth specimens are dulled for 30 seconds in 0.2 N HCl. These specimens have previously been mounted in a Wood's metal base and the exposed labial surface flattened slightly with a surface grinder. A flat surface is necessary in order to obtain reliable reflectance readings. After dulling, one specimen is mounted securely into place in the reservoir, while the other is mounted into the holder that is attached to the shaft above the reservoir. Next, the two paddles are placed on each side of the teeth. The reservoir is then clamped into place and the chewing counter is set at zero. The gum under investigation is then presoftened by the operator and placed in the reservoir between the teeth and paddles. Approximately 20 grams of the presoftened gum bolus are required for each test. All saliva arising from the softening process is collected and placed in the reservoir. When the temperature has stabilized at 37° C., the machine is turned on and mastication begins. During each stroke the gum is "chewed" between the occluding upper and lower teeth. The upper shaft is so designed that upon occlusion a rocking action takes place in order to simulate the shearing effect achieved during normal mastication in the human mouth. After each chewing cycle, the paddles push the chewed gum back into position over the lower tooth in preparation for the next chewing cycle.

After the gum is evaluated for a set number of chewing cycles, the tooth specimens are removed and the resulting level of polish determined by means of a reflectometer. The reflectometer is especially designed to emit a beam of light at a 45° angle onto the flattened tooth surface. The more highly polished the surface, the more the incident light beam will be deflected to a photodetector mounted at the complimentary 45° angle. The enamel polish score is compared to that of a white carrara standard. The reflectance of the white carrara is arbitrarily set at 100, while no reflectance in total darkness is set at 0. The average polish score observed for the baseline acid-dulled teeth is 18.

This mastication device can also be adapted to evaluate the abrasion potential of chewing gums. For abrasion testing, smooth, flattened pieces of enamel mounted in Wood's metal are used. A microscratch is made on the surface of each specimen and then an initial surface profile is obtained using a profilometer. The specimens are then treated for a set number of chewing cycles with the chewing gum under investigation. After treatment, a second surface profile is obtained for each specimen. By comparing the scratch depths of the profile traces before and after treatment, the amount and depth of enamel abraded can be calculated.

Using the foregoing technique, enamel polishing scores were determined for a number of commercially available chewing gums containing calcium carbonate or talc as filler components in the gum base. Polishing scores for these commercial gums are reported in Table 2, which demonstrates that these gums do not effectively polish the dental enamel to any significant degree.

TABLE 2

| ENAMEL POLISH OF COMMERCIAL CHEWING GUMS | |
|---|---|
| Commercial Chewing Gum Brand | Enamel Polish* |
| Trident | 30 ± 4 |
| Beech-nut Peppermint | 47 ± 10 |
| Adams Sour | 31 ± 5 |
| Wrigley's Spearmint | 28 ± 7 |
| Dentyne | 51 ± 7 |
| Wrigley's Doublemint | 35 ± 3 |
| Care-Free | 47 ± 6 |

*Mean ± standard deviation after 1000 chewing cycles, n = 6

Polishing scores were also determined for a number of chewing gums containing various concentrations of calcined kaolin particles either as a filler component or as an add-on ingredient to the chewing gum. In addition, certain of the experimental gums measured also contained 3% adipic acid as well. These data are reported in Table 3. The data in Table 3 show that slightly better polishing levels were obtained where the calcined kaolin particles were provided as an add-on ingredient and that polishing scores increased with increasing concentration of kaolin. The most dramatic increases in polish were observed in the specimens containing adipic acid in combination with calcined kaolin.

TABLE 3

EFFECT OF CALCINED KAOLIN CONCENTRATION OF ENAMEL POLISH

| Amount of Calcined Kaolin Present | | | | |
|---|---|---|---|---|
| As Filler | As Add-on | Total | Acid Present | Enamel Polish* |
| 0 | 0 | 0 | None | 31 ± 5 |
| 0 | 5.0% | 5.0% | 3% Adipic | 92 ± 8 |
| 0 | 10.0% | 10.0% | 3% Adipic | 105 ± 4 |
| 0 | 20.0% | 20.0% | 3% Adipic | 108 ± 4 |
| 7.67% | 0 | 7.67% | None | 59 ± 3 |
| 0 | 7.67% | 7.67% | None | 64 ± 10 |
| 7.67% | 10.0% | 17.67% | None | 69 ± 7 |
| 7.67% | 20.0% | 27.67% | None | 73 ± 7 |
| 7.67% | 10.0% | 17.67% | 3% Adipic | 100 ± 10 |
| 7.67% | 0 | 7.67% | 3% Adipic | 87 ± 8 |

*Mean ± standard deviation after 1000 chewing cycles, n = 6

A series of studies was also conducted in order to determine the effect of variations in the concentration of the acid components. Table 4 reports polishing scores for a series of calcined kaolin-containing gum where the content of adipic acid varied between 0 and 3%. These data demonstrate that the progressive increase in the adipic acid concentration up to about 3% resulted in a doubling of the enamel polishing score.

TABLE 4

EFFECT OF ADIPIC ACID CONCENTRATION ON ENAMEL POLISH OF CHEWING GUMS CONTAINING CALCINED KAOLIN

| Amount of Adipic Acid in Chewing Gum (%) | Aqueous pH** | Enamel Polish* |
|---|---|---|
| 0.00 | 5.8 | 50 ± 6 |
| 0.35 | 3.7 | 57 ± 6 |
| 1.00 | 3.2 | 88 ± 6 |
| 1.78 | 3.1 | 80 ± 7 |
| 3.00 | 2.9 | 100 ± 10 |

*Mean ± standard deviation, n = 6, 1000 chewing cycles
**1.0 gram of gum mixed with 10 ml redistilled water Table 5 reports comparable acid concentration data for lactic acid. An increase in the amount of lactic acid in the calcined kaolin-containing gum correspondingly increased enamel polish. However, above the 3% concentration (pH=2.6) level, enamel polish dropped significantly due to acid dulling of the tooth.

TABLE 5
EFFECT OF LACTIC ACID CONCENTRATION ON ENAMEL POLISH OF CHEWING GUMS CONTAINING CALCINED KAOLIN

| Amount of Lactic Acid in Chewing Gum (%) | Aqueous pH** | Enamel Polish* |
|---|---|---|
| 0.00 | 5.8 | 50 ± 6 |
| 0.35 | 3.4 | 59 ± 7 |
| 0.54 | 3.3 | 64 ± 6 |
| 0.61 | 3.3 | 68 ± 4 |
| 0.70 | 3.1 | 80 ± 3 |
| 0.86 | 3.0 | 87 ± 9 |
| 1.00 | 2.8 | 80 ± 4 |
| 1.07 | 2.8 | 83 ± 3 |
| 1.50 | 2.7 | 86 ± 3 |
| 2.25 | 2.6 | 87 ± 4 |
| 3.25 | 2.5 | 36 ± 3 |

*Mean ± standard deviation, n = 6, 1000 chewing cycles
**1.0 gram of gum mixed with 10 ml redistilled water Table 6 reports acid concentration data for phosphoric acid. Once again, an increase in the amount of acid increases enamel polish. At 0.357% phosphoric acid concentration, no appreciable drop in enamel polish was observed which indicates that still higher concentrations of the acid could be used without harmful demineralization of the teeth occurring.

TABLE 6
EFFECT OF PHOSPHORIC ACID CONCENTRATION ON ENAMEL POLISH OF CHEWING GUMS CONTAINING CALCINED KAOLIN

| Amount of Phosphoric Acid in Chewing Gum (%) | Aqueous pH** | Enamel Polish* |
|---|---|---|
| 0.00 | 5.8 | 50 ± 6 |
| 0.150 | 3.4 | 71 ± 10 |
| 0.179 | 3.1 | 98 ± 5 |
| 0.193 | 3.1 | 97 ± 6 |
| 0.229 | 3.0 | 98 ± 9 |
| 0.250 | 2.9 | 97 ± 9 |
| 0.285 | 2.8 | 99 ± 5 |
| 0.357 | 2.8 | 96 ± 4 |

*Mean ± standard deviation, n = 6, 1000 chewing cycles
**1.0 gram of gum mixed with 10 ml water The ability of other acids to enhance the enamel polishing efficacy of calcined kaolin chewing gums has also been demonstrated. Table 7 reports data for a series of calcined kaolin containing gums containing 1% of citric acid, fumaric acid, tartaric acid, malic acid, succinic acid, ascorbic acid, glutaric acid, adipic acid and lactic acid, respectively. Table 8 reports similar data for 3 M concentrations of inorganic acids. In all cases polish was improved relative to the gum containing no acid although the results were marginal in the case of fumaric acid because of its limited solubility. Similarly, boric acid, a very weak acid, provided minimal polishing.

TABLE 7
EFFECT OF VARIOUS CARBOXYLIC ACIDS ON ENAMEL POLISH OF CHEWING GUMS CONTAINING CALCINED KAOLIN

| Type of Acid* | Aqueous pH** | Enamel Polish*** |
|---|---|---|
| None | 5.8 | 50 ± 6 |
| Citric | 2.7 | 74 ± 4 |
| Fumaric | 2.9 | 57 ± 8 |
| Tartaric | 2.7 | 80 ± 8 |
| Malic | 2.8 | 80 ± 7 |
| Succinic | 3.2 | 84 ± 4 |
| Ascorbic | 3.2 | 89 ± 10 |
| Glutaric | 3.2 | 90 ± 9 |

TABLE 7-continued
EFFECT OF VARIOUS CARBOXYLIC ACIDS ON ENAMEL POLISH OF CHEWING GUMS CONTAINING CALCINED KAOLIN

| Type of Acid* | Aqueous pH** | Enamel Polish*** |
|---|---|---|
| Adipic | 3.2 | 88 ± 6 |
| Lactic | 2.8 | 80 ± 4 |

*Present in the chewing gum at a 1% concentration; calcined kaolin present at 10%.
**1.0 gram of gum mixed with 10 ml redistilled water.
***Mean ± standard deviation, n = 6, 1000 chewing cycles.

TABLE 8
EFFECT OF VARIOUS INORGANIC ACIDS ON ENAMEL POLISH OF CHEWING GUMS CONTAINING CALCINED KAOLIN

| Type of Acid* | Aqueous pH** | Enamel Polish*** |
|---|---|---|
| None | 5.8 | 50 ± 6 |
| Phosphoric | 3.2 | 88 ± 4 |
| Hydrochloric | 3.1 | 87 ± 9 |
| Nitric | 3.2 | 94 ± 9 |
| Perchloric | 3.3 | 86 ± 4 |
| Sulfuric | 3.2 | 106 ± 4 |
| Boric | 4.9 | 70 ± 3 |

*Present in the chewing gum at a concentration equivalent to 3.0 M; calcined kaolin present at 10%.
**1.0 gram of gum mixed with 10 ml of redistilled water.
***Mean ± standard deviation, n = 6, 1000 chewing cycles.

It has also been demonstrated that mixtures of acids producing an aqueous pH in the range of about 2.6 to 3.3 can be utilized to bring about the enhanced enamel polishing capability as shown by the data in Table 9.

TABLE 9
EFFECT OF ACID MIXTURES ON ENAMEL POLISH OF CHEWING GUMS CONTAINING CALCINED KAOLIN

| Mixture of Acids in Chewing Gum* | Aqueous** pH | Enamel Polish*** |
|---|---|---|
| 0.5% adipic + 0.5% lactic | 3.0 | 92 ± 14 |
| 0.5% glutaric + 0.5% citric | 2.9 | 77 ± 5 |
| 0.8% ascorbic + 0.2% malic | 3.0 | 80 ± 4 |
| 0.1% phosphoric + 0.13% hydrochloric | 2.9 | 105 ± 7 |
| 0.1% nitric + 0.13% perchloric | 3.2 | 88 ± 7 |
| 0.09% sulfuric + 1.0% 3M boric | 3.4 | 91 ± 7 |
| 0.01% phosphoric + 1.0% adipic | 3.2 | 86 ± 5 |
| 0.13% hydrochloric + 1.0% lactic | 2.8 | 84 ± 10 |
| 0.09% sulfuric + 1.0% citric | 2.6 | 40 ± 7 |
| 0.18% $H_3PO_4$ + 0.07% $Ca(H_2PO_4)_2$ | 3.2 | 93 ± 12 |
| 0.14% $NaHSO_3$ + 0.14% $Ca(H_2PO_4)_2$ | 3.1 | 94 ± 10 |
| 0.18% $H_3PO_4$ + 0.14% $Ca(H_2PO_4)_2$ | 3.1 | 87 ± 6 |
| 0.129% $H_3PO_4$ + 0.085% $Na_2H_2P_2O_7$ + 0.085% $NaH_2PO_4$ | 3.3 | 87 ± 6 |
| 0.135% $H_3PO_4$ + 0.085% $Na_2H_2P_2O_7$ + 0.085% $NaH_2PO_4$ | 3.2 | 81 ± 3 |

*Chewing gums contained 10% calcined kaolin.
**1.0 gram of gum mixed with 10 ml of redistilled water.
***Mean ± standard deviation, n = 6, 1000 chewing cycles.

The effect of the kaolin calcination temperatures has also been investigated. A series of chewing gums containing kaolin calcined at various temperatures were prepared and evaluated for polish in accordance with the previously described procedure. Enamel polishing scores are reported in Table 10.

TABLE 10
EFFECT OF CALCINATION TEMPERATURE ON THE ENAMEL POLISH OF CHEWING GUM CONTAINING CALCINED KAOLIN

| Calcination Temperature of Kaolin Present in the Chewing Gum* | Enamel Polish** |
|---|---|
| uncalcined | 37 ± 5 |
| 900° C. | 76 ± 7 |
| 1000° C. | 100 ± 8 |
| 1100° C. | 105 ± 4 |
| 1200° C. | 108 ± 9 |

*The kaolin (median particle size: 0.4 micrometers) was present in the gum at a 10% concentration along with 3% adipic acid.
**Mean ± standard deviation after 1000 chewing cycles, n = 6

Chewing gums containing uncalcined kaolin and an acid source did not polish any better than conventional chewing gums, and only moderate improvement was observed with kaolin calcined at 900° C. However, at calcination temperatures above 1000° C., significant enamel polish improvements were obtained. Increasing calcination temperature beyond 1100° C. resulted in little additional enamel polishing improvement.

The effect of calcination temperature on abrasion has also been studied. Enamel and dentin abrasion scores were determined using the American Dental Association toothbrushing abrasion method, and these data are presented in Table 11. For comparative purposes, data are also given for calcium pyrophosphate, the standard dental abrasive pursuant to that procedure.

TABLE 11
EFFECT OF KAOLIN CALCINATION TEMPERATURE ON DENTIN AND ENAMEL ABRASION

| Calcination Temperature of Kaolin* | Abrasion Score** | |
|---|---|---|
| | Dentin | Enamel |
| 1000° C. | 243 ± 39 | 499 ± 61 |
| 1050° C. | 249 ± 30 | 509 ± 37 |
| 1100° C. | 327 ± 43 | 618 ± 48 |
| 1200° C. | 859 ± 40 | 1086 ± 140 |
| Calcium pyrophosphate control | 475 | 500 |

*Median particle size: 0.6 micrometers.
**Mean ± standard deviation, n = 8.

The data of Table 11 demonstrate that kaolin particles calcined in the range of about 1000°–1100° C. have dentin and enamel abrasions scores comparable to that of the standard calcium pyrophosphate abrasive, and kaolin particles calcined in this range are accordingly preferred in accordance with this invention. As shown in Table 11, higher calcination temperatures increase abrasion and should be avoided for that reason.

Further studies were undertaken in order to determine the effect of calcined kaolin particle size on the enamel polish achievable with the chewing gums. A series of chewing gum samples containing an acid source and calcined kaolin particles having median sizes ranging from 0.2 micrometers up to 9.5 micrometers were prepared, and enamel polishing scores measured in accordance with the described procedure. The data, which are reported in Table 12, demonstrate that, with increasing particle size, polishing effectiveness increases.

TABLE 12
EFFECT OF PARTICLE SIZE ON THE ENAMEL POLISH OF CHEWING GUMS CONTAINING CALCINED KAOLIN

| Median Particle Size of Calcined Kaolin (micrometers) | Enamel Polish** |
|---|---|
| 0.2 | 95 ± 6 |
| 0.7 | 91 ± 13 |
| 1.8 | 92 ± 3 |
| 2.4 | 102 ± 11 |
| 9.5 | 101 ± 4 |

*The kaolins (calcined at 1050° C.) were present in the chewing gums at a concentration of 10% along with 3% adipic acid.
**Mean ± standard deviation after 1000 chewing cycles, n = 6.

While larger median size particles appear to polish somewhat better, a risk of undue abrasion and scratching occurs with larger size particles as shown by the data in Table 13.

TABLE 13
EFFECT OF CALCINED KAOLIN PARTICLE SIZE ON DENTIN AND ENAMEL ABRASION

| Median Particle Size of Calcined Kaolin* (micrometers) | Abrasion Score** | |
|---|---|---|
| | Dentin | Enamel |
| 0.3 | 195 ± 13 | 432 ± 38 |
| 0.4 | 199 ± 20 | 473 ± 63 |
| 0.5 | 217 ± 9 | 444 ± 38 |
| 0.9 | 245 ± 30 | 596 ± 56 |
| 1.7 | 478 ± 23 | 732 ± 87 |
| Calcium pyrophosphate control | 475 | 500 |

*Calcined at 1050° C.
**Mean ± standard deviation, n = 8. These are radioactive dentin and enamel abrasion scores obtained using the ADA toothbrushing abrasion method.

The data of Table 13 demonstrate that utilization of calcined kaolin particles having a median particle size greater than about 2.0 micrometers may cause harmful abrasion. Consistent with this invention, the largest median particle size calcined kaolin that can be employed without causing harmful abrasion should be utilized so that maximum cleaning is achieved along with polishing of the enamel.

The abrasion data in Tables 11 and 13 were obtained using the American Dental Association toothbrush abrasivity method which involved brushing radioactive enamel and dentin specimens with slurries of abrasive. In order better to examine the abrasion potential of chewing gums in accordance with this invention, a further abrasion study was performed utilizing the mastication machine previously described. In this manner, it has been demonstrated that neither acidified calcined kaolin-containing chewing gums nor commercial control chewing gums removed significant surface enamel of teeth after 2000 chewing cycles. These data are reported in Table 14.

TABLE 14
ENAMEL ABRASION OF CHEWING GUM CONTAINING CALCINED KAOLIN

| Chewing Gum | n | Amount of Surface Enamel Abraded (micrometers)** |
|---|---|---|
| Commercial Control (CaCO$_3$ as filler) | 8 | 0.01 ± 0.05 |
| Calcined Kaolin* | 8 | 0.02 ± 0.08 |

*Present in the chewing gum at a concentration of 9.6%; calcination temperature: 1050° C.; median particle size: 1.8 micrometers.
**Mean ± standard deviation after 2000 chewing cycles. Student t-test demonstrated no significant difference in abrasion between the two chewing gums.

A variety of different chewing gum and bubble gum bases were employed to formulate chewing gums containing calcined kaolin particles and acid in accordance with this invention. The test gums were evaluated for enamel polish, with the results being presented in Table 15. Because it is essential to employ an acid source in a gum in accordance with this invention to achieve the enhanced polishing desired, gum bases employing calcium carbonate fillers can not be used. Such gums crumble upon chewing due to the reaction of calcium carbonate with the acid, thus counteracting the polishing effect as shown by the data in Table 15. However, using gum bases containing talc as a filler resulted in chewing gum producing excellent levels of enamel polish.

TABLE 15

EFFECT OF CHEWING GUM BASE ON THE ENAMEL POLISH OF CHEWING GUMS CONTAINING CALCINED KAOLIN

| Type of Chewing Gum Base | Filler Present in Base | Chewing Texture of the Gum* | Enamel Polish** |
|---|---|---|---|
| Paloja Bubble T | talc | soft | 88 ± 12 |
| Ladco Bubble T | talc | moderate | 90 ± 10 |
| Grande Bubble T | talc | very film | 105 ± 4 |
| Global Bubble | CaCO$_3$ | crumbly | 62 ± 11 |
| Grande Bubble | CaCO$_3$ | crumbly | 52 ± 9 |
| Paloja T | talc | firm | 92 ± 3 |
| Nova T | talc | very firm | 101 ± 7 |

*All gums contained 10% calcined kaolin and 3% adipic acid.
**Mean ± standard deviation, 1000 chewing cycles, n = 6.

In addition to the foregoing in vitro laboratory studies demonstrating the characteristics of the present invention, human clinical studies have also been performed in order to determine the ability of chewing gums in accordance with this invention to clean dental plaque from the teeth.

Sixteen male children between the ages of eight and fourteen were instructed to refrain from toothbrushing for twenty-four hours in order to accumulate dental plaque on the teeth prior to evaluation. The initial baseline plaque scores of each subject was then determined. The plaque was disclosed by placing three drops of 0.75% fluorescein disclosant under the subject's tongue and instructing the subject to spread the dye over all teeth using his tongue. The subject was then given one-half ounce of distilled water and instructed to rinse and expectorate, thereby removing any of the excess plaque disclosing solution. Next, the buccal (or labial) and lingual surfaces of all teeth were scored for plaque using the Quigley-Hein scoring index In order for the disclosed plaque to be visible, it is necessary to use a special narrow band, white light energy beam (Plak-Lite) for illuminating the mouth. This light causes all areas of plaque on the teeth to radiate a bright fluorescent yellow color.

After scoring the initial plaque, the subjects were randomly distributed into two groups. One group was given a gum containing 9.5% calcined kaolin (3.0% as filler, 6.5% as add-on) and 0.8% lactic acid, while the other was given a control gum without the calcined kaolin or acid. After the children chewed the gum for fifteen minutes under supervision, the plaque was rescored using the method mentioned previously. The amount of plaque removed was determined by a comparison of the initial and final examination scores and the efficacy expressed in terms of the percent of plaque removed. Separate plaque reduction scores were calculated for all teeth and also for just the posterior teeth. A matched-pair statistical analysis was performed in order to determine the significance of the results.

The results, which are reported in Table 16, demonstrated that a control chewing gum not containing calcined kaolin failed to remove plaque from the teeth while the chewing gum containing kaolin and acid removed 8.2% of the dental plaque after 15 minutes of chewing. If only the posterior dentition is considered (where chewing gum is predominantely masticated), a plaque reduction score of 12.4% is obtained for the calcined kaolin gum. Both plague reduction scores were statistically significant. Thus, this study demonstrated that a 3.0 gram piece of acid-containing calcined kaolin chewing gum was capable of removing dental plaque from tooth surfaces, especially those in the posterior region of the mouth.

TABLE 16

CLEANING EFFECT OF THE ACID-CONTAINING CALCINED KAOLIN CHEWING GUM

| | Mean Plaque Score (All Teeth) | | | Mean Plaque Score (Posterior Teeth) | | |
|---|---|---|---|---|---|---|
| Treatment | Before Chewing | After Chewing | Plaque Reduction | Before Chewing | After Chewing | Plaque Reduction |
| Control Chewing Gum | 2.29 ± 0.34 | 2.30 ± 0.30 | −0.4% | 2.12 ± 0.23 | 2.10 ± 0.26 | 0.9% |
| Kaolin Chewing Gum | 2.44 ± 0.39 | 2.24 ± 0.43 | 8.2%* | 2.18 ± 0.38 | 1.91 ± 0.36 | 12.4%* |

*Statistically significant at $p < 0.05$.

A second clinical study was performed to evaluate dental plaque cleaning of two different sized pieces of acid-containing calcined kaolin chewing gums. A 2.5 gram stick of the calcined kaolin gum was compared with a 7.0 gram chunk. The methodology used was identical to that outlined in the first clinical study with the following exceptions. In this study, the children developed plaque on their teeth for two days instead of one, and only the posterior teeth were scored for plaque since the first clinical demonstrated minimal effect on the anterior teeth.

The results of this clinical are presented in Table 17. Both the 2.5 gram piece and the 7.0 gram piece of acid-containing calcined kaolin chewing gum significantly removed dental plaque from the teeth. However, the 24.3% reduction in plaque produced by chewing the 7.0 gram size piece for 15.0 minutes was statistically better than the 14.2% plaque reduction observed for the 2.5 gram size piece. The larger size piece is capable of coming into contact with more areas of the teeth covered with plaque, especially the plaque located around the gingival margin.

TABLE 17

IN VIVO CLEANING EFFECT OF TWO DIFFERENT SIZE PIECES OF ACID-CONTAINING KAOLIN CHEWING GUM

| Treatment Group | No. of Subjects | Mean Plaque Score (Posterior Teeth) | | | |
|---|---|---|---|---|---|
| | | Before Chewing | After Chewing | Plaque Reduction | Statistical Significance |
| 2.5 gram piece of gum* | 10 | 2.46 ± 0.56 | 2.11 ± 0.53 | 14.2% | p <0.01 |
| 7.0 gram piece of gum* | 10 | 2.59 ± 0.43 | 1.96 ± 0.43 | 24.3%** | p <0.01 |

*The gum contained 9.5% calcined kaolin polishing - cleaning agent (3.0% filler, 6.5% as add-on) and 0.8% lactic acid and was chewed for 15 minutes.
**Note: the 7.0 gram piece significantly removed more plaque than the 2.5 gram piece at p <0.05.

From the foregoing it can be seen that the chewing gum compositions in accordance with this invention have the ability to impart a very high degree of polish to dental enamel. By regularly chewing with such a gum, one not only polishes the teeth but also reduces dental plaque formation thereon. In combination with other recommended oral hygiene techniques (e.g. daily toothbrushing and periodic professionally administered prophylaxis treatments), use of the chewing gums with this invention substantially enhance the overall oral health of the user.

We claim:

1. A chewing gum capable of cleaning and imparting a high degree of polish to the teeth consisting essentially of:
    a chewing gum base;
    a non-toxic source of acid present in an amount sufficient to produce an aqueous pH of from about 2.6 to about 3.3 when measured in a solution with a concentration of 0.1 gram by total gum weight of said chewing gum to 1 milliliter of demineralized water; and
    about 1–50% by total gum weight of calcined kaolin particles, the median diameter of the particles being about 2 micrometers or less, substantially all of the particles being less than about 20 micrometers in diameter.

2. A chewing gum, as claimed in claim 1, wherein the kaolin particles are at least in part provided as an add-on ingredient to the chewing gum.

3. A chewing gum, as claimed in claim 1, wherein the kaolin particles are provided at least in part as a filler constituent in the chewing gum base.

4. A chewing gum, as claimed in claim 1, wherein acidophilic ingredients are substantially excluded from the gum.

5. A chewing gum, as claimed in claim 1, wherein the kaolin particles are calcined at a temperature lying in the range of about 1000°–1100° C.

6. A chewing gum, as claimed in claim 1, wherein the calcined kaolin particles are provided at a level of about 5–15% by total gum weight.

7. A chewing gum, as claimed in claim 1, wherein the non-toxic source of acid is a member selected from the group consisting of citric acid, fumaric acid, tartaric acid, malic acid, succinic acid, ascorbic acid, glutaric acid, adipic acid, lactic acid, phosphoric acid, perchloric acid, nitric acid, sulfuric acid, boric acid, hydrochloric acid, hydroxyacetic acid, salts thereof, and mixtures thereof.

8. A chewing gum, as claimed in claim 1, wherein the non-toxic source of acid is a mixture of hydroxyacetic acid and phosphoric acid.

9. A method of imparting a high degree of polish to the dental enamel comprising regularly chewing of a chewing gum consisting essentially of:
    a chewing gum base;
    a non-toxic source of acid present in an amount sufficient to produce an aqueous pH of from about 2.6 to about 3.3 when measured in a solution with a concentration of 0.1 gram by total gum weight of said chewing gum to 1 milliliter of demineralized water; and
    about 1–50% by total gum weight of calcined kaolin particles, the median diameter of the particles being about 2 micrometers or less, substantially all of the particles being less than about 20 micrometers in diameter.

10. A method of removing dental plaque from on the teeth and inhibiting its reformation comprising regularly chewing of a chewing gum consisting essentially of:
    a chewing gum base;
    a non-toxic source of acid present in an amount sufficient to produce an aqueous pH of fromm about 2.6 to about 3.3 when measured in a solution with a concentration of 0.1 gram by total gum weight of said chewing gum to 1 milliliter of demineralized water; and
    about 1–50% by total gum weight of calcined kaolin particles, the median diameter of the particles being about 2 micrometers or less, substantially all of the particles being less than about 20 micrometers in diameter.

11. A method, as claimed in claims 9 or 10, wherein the non-toxic source of acid is a member selected from the group consisting of citric acid, fumaric acid, tartaric acid, malic acid, succinic acid, ascorbic acid, glutaric acid, adipic acid, lactic acid, phosphoric acid, perchloric acid, nitric acid, sulfuric acid, boric acid, hydrochloric acid, hydroxyacetic acid, salts thereof, and mixtures thereof.

12. A method, as claimed in claims 9 or 10, wherein the non-toxic source of acid is a mixture of hydroxyacetic acid and phosphoric acid.

* * * * *

UNITED STATES PATENT AND TRADEMARK OFFICE
CERTIFICATE OF CORRECTION

PATENT NO. : 4,400,372

DATED : August 23, 1983

INVENTOR(S) : Joseph C. Muhler, et al.

It is certified that error appears in the above—identified patent and that said Letters Patent is hereby corrected as shown below:

Col. 5, line 50, "kaolin" should be --calcined kaolin--.

Col. 11, line 16, "1100°," should be --1100° C.,--.

Col. 12, line 23, "accomodating" should be --accommodating--.

Col. 12, line 27, "accomodate" should be --accommodate--.

Col. 16, line 44, "0.01%" should be --0.1%--.

Col. 16, line 63, "temperatures" should be --temperature--.

Col. 17, line 67, in Table 12, "of Calcined Kaolin (micrometers)" should be --of Calcined Kaolin* (micrometers)--.

Col. 18, line 5, in Table 12, "of Calcined Kaolin (micrometers)" should be -of Calcined Kaolin* (micrometers)--.

Col. 19, line 20, "very film" should be --very firm--.

Col. 19, line 52, "accumulate" should be --accummulate--.

UNITED STATES PATENT AND TRADEMARK OFFICE
CERTIFICATE OF CORRECTION

PATENT NO. : 4,400,372

DATED : August 23, 1983

INVENTOR(S) : Joseph C. Muhler, et al.

It is certified that error appears in the above—identified patent and that said Letters Patent is hereby corrected as shown below:

Col. 19, line 63, "index In" should be --index. In--.

Col. 22, line 39, "fromm" should be --from--.

Signed and Sealed this

Thirteenth Day of December 1983

[SEAL]

Attest:

GERALD J. MOSSINGHOFF

Attesting Officer

Commissioner of Patents and Trademarks